US008486256B2

(12) United States Patent
Botte et al.

(10) Patent No.: US 8,486,256 B2
(45) Date of Patent: Jul. 16, 2013

(54) ELECTROCHEMICAL TECHNIQUE TO MEASURE CONCENTRATION OF MULTIVALENT CATIONS SIMULTANEOUSLY

(75) Inventors: Gerardine G. Botte, Athens, OH (US); Xin Jin, Athens, OH (US)

(73) Assignee: Ohio University, Athens, OH (US)

( * ) Notice: Subject to any disclaimer, the term of this patent is extended or adjusted under 35 U.S.C. 154(b) by 505 days.

(21) Appl. No.: 12/299,782

(22) PCT Filed: May 8, 2007

(86) PCT No.: PCT/US2007/011087
§ 371 (c)(1),
(2), (4) Date: Apr. 21, 2009

(87) PCT Pub. No.: WO2007/133534
PCT Pub. Date: Nov. 22, 2007

(65) Prior Publication Data
US 2010/0032320 A1    Feb. 11, 2010

Related U.S. Application Data

(60) Provisional application No. 60/798,691, filed on May 8, 2006.

(51) Int. Cl.
*G01N 27/26* (2006.01)
(52) U.S. Cl.
USPC ............... 205/789.5; 204/416; 205/775
(58) Field of Classification Search
USPC ............... 204/400, 416, 417, 412; 205/81, 205/789, 793.5, 794, 795.4, 775, 792, 789.5
See application file for complete search history.

(56) References Cited

U.S. PATENT DOCUMENTS

| | | | |
|---|---|---|---|
| 4,725,339 A | 2/1988 | Bindra et al. | |
| 5,223,118 A * | 6/1993 | Sonnenberg et al. | 205/81 |
| 5,234,568 A | 8/1993 | Tomita | |
| 6,106,692 A * | 8/2000 | Kunimatsu et al. | 205/775 |
| 6,572,753 B2 | 6/2003 | Chalyt et al. | |

FOREIGN PATENT DOCUMENTS

JP    1047942 A    2/1989

OTHER PUBLICATIONS

"9.3.2 Solution of the Convective-Diffusion Equation". Bard, Allen J., and Larry R. Faulkner. Electrochemical Methods: Fundamentals and Applications. New York [u.a.: Wiley, 2001. Print.*
Kissinger, Peter T., and William R. Heineman. Laboratory Techniques in Electroanalytical Chemistry. New York [etc.: Marcel Dekker, 1996. 614.*

(Continued)

*Primary Examiner* — Keith Hendricks
*Assistant Examiner* — Kourtney S Carlson
(74) *Attorney, Agent, or Firm* — Wood, Herron & Evans, LLP

(57) ABSTRACT

Methods and systems for simultaneously measuring concentration of two or more different cations in solution. The methods include the steps of applying a steady state polarization technique to a solution comprising two or more different cations; measuring the limiting currents of the solution; and correlating the limiting currents with the concentration of the different cations. The system includes a working electrode; a potentiostat; a counter electrode; a reference electrode; a solution comprising different cations to be analyzed; and a model for correlating the limiting currents with the concentration of the pair cations. The working electrode may be any electrode compatible with the media, including noble metals, carbon, or combinations thereof. In some embodiments, the working electrode is a rotating disk electrode (RDE).

6 Claims, 7 Drawing Sheets

OTHER PUBLICATIONS

International Search Report, International Application No. PCT/US07/11087, mailed Feb. 12, 2008, 3pp.

JP 1047942—English-language abstract obtained from http://ep.espacenet.com/, Feb. 22, 1989.

* cited by examiner

ELECTROCHEMICAL TECHNIQUE TO MEASURE CONCENTRATION OF MULTIVALENT CATIONS SIMULTANEOUSLY

CROSS-REFERENCE TO RELATED APPLICATIONS

This application is a U.S. National Stage Entry of International Application No. PCT/US2007/011087, filed May 8, 2007, which is incorporated by reference in its entirety, which claims benefit to U.S. Provisional Patent Application No. 60/798,691 filed May 8, 2006, the entirety of which is incorporated herein, by reference.

BACKGROUND OF THE INVENTION

Iron ion is one of the most common and important metal ions in nature, and its valences are bivalent and trivalent. Simultaneously analyzing the two valences is important not only for biochemistry and environmental chemistry, but also in many scientific and industrial fields. For biogeochemical cycles which determine the environmental availability of trace elements at the sediment/water interface, pushes towards the development of analytical methods which might be sensitive, of practical use and able to give information on iron speciation, in particular with respect to its oxidation state. So far, atomic absorption spectroscopy (AAS), Ion chromatography (IC), inductively coupled plasma (ICP)-Atomic Emission Spectrometry (AES) and/or mass spectrometry have been generally known as analytical techniques for metal ions; however, these methods can not distinguish any difference in the metal valences. For example, the principle of AAS is to use the absorption of light to measure the concentration of gas-phase atoms which depend on the properties of metal, not ion. IC is also a very common method, but its principle is: Ions in solution of a certain concentration can conduct electrical charges, with a linear correlation between the concentration of the ions and the current conducted. Also this method needs pretreatment and special chelating reagent when used for different ions determination. For those methods, the process becomes very complex and expensive when they are used for determination of Fe (II)/Fe (III) concentration in the same solution. The common procedures for those methods are: first, Fe (II) is complexed with specific chelating agents, and then measured by this method. Fe (III) is subsequently reduced to Fe (II) and the total iron is determined, and then yielding the concentration of Fe (III). Those methods need to measure the sample twice and the instrument is expensive. Other methods such as: Solid Phase Colorimetry based on Tristimulus Chromaticity Diagram (SPC-TCD), Potentiometry and ion-exchange voltammetry (PIEV), differential-pulse cathodic stripping voltammetry (DPCSV), and Cyclic and Multiple Square-Wave Voltammetry (CMSWV) are not as expensive as AAS or IC, but they can only be used for total iron ion determination (only one of the species) and most of them are limited by tedious procedure.

Accordingly, a need exists for new methods for measuring multivalent cations in solution simultaneously. A further need exists for a system that employs that method.

SUMMARY OF THE INVENTION

Provided herein are methods for simultaneously measuring concentration of two or more different cations in solution. The methods include the steps of applying a steady state polarization technique to a solution comprising two or more different cations; measuring the limiting currents of the solution; and correlating the limiting currents with the concentration of the different cations. The methods are useful for combinations of multivalent cations in solution as well as combinations of multiple metal cations in solution.

Also provided is a system for simultaneously measuring concentration of two or more different cations in solution. The system includes a working electrode; a potentiostat; a counter electrode; a reference electrode; a solution comprising different cations to be analyzed; and a model for correlating the limiting currents with the concentration of the pair cations. The working electrode may be any electrode compatible with the media, including noble metals, carbon, or combinations thereof. In some embodiments, the working electrode is a rotating disk electrode (RDE).

DETAILED DESCRIPTION OF THE INVENTION

Figure 1:
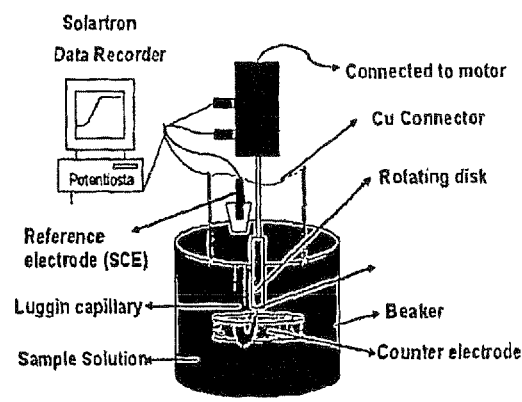
FIG. 1 shows a simple representative structure of the rotating disk electrode (RDE).

Provided herein is a new technique to measure the concentration of multivalent cations in solution simultaneously. Examples of multivalent cations include the following pairs: Fe(II)/Fe(III), As(III)/As(V), Se(IV)/Se(VI), Cr(VI)/Cr(III), and Sb(III)/Sb(V). The technique has been called EM2C2 (Electrochemical Measurement of Multivalent Cations Concentration). The method consists of using a steady state polarization technique, where the developed limiting currents are measured and they are related to the concentration of the cations (analyte) present in solution. A model has been developed that correlates the limiting currents with the concentration of the pair cations, so that we can easily calculate the concentration in the solution of both of the multivalent cations simultaneously.

Further provided is a system for using the technique described herein. The system comprises a working electrode comprising a rotating disk electrode (RDE); a potentiostat; a counter electrode; a reference electrode; and a solution comprising multivalent cations to be analyzed; and a model for correlating the limiting currents with the concentration of the pair cations.

This technique finds its purpose in the following applications (but not limited to): Wastewater and sediment treatment company (environmental applications where it is necessary to know the concentration of both species); chemical manufacturing wherein cations in products and/or processes must be monitored; research and development company that depends on knowing multiple cation concentrations to develop new products; laboratories that work with characterization of samples. Some specific examples include (but are not limited to): the food industry wherein iron ion concentration is important; and in coal electrolysis, the iron ion determination will help to determine the coal electrolysis mechanism with Fe (II) and Fe (III) as additives.

The methods described herein may be used to simultaneously measure concentrations of different ions in a single solution, including combinations of different metal ions as well as combinations of ions of different oxidation states of a single metal, and combinations thereof. While these methods may be adapted for virtually any multivalent cations, some exemplary multivalent cations include, but are not limited to: Fe(II)/Fe(III), As(III)/As(V), Se(IV)/Se(VI), Cr(VI)/Cr(III), and Sb(III)/Sb(V). The couple Fe(II)/Fe(III) has been chosen as a specific example to describe the problem and the solution though it should be recognized by those skilled in the art that the methods may easily be adapted to other ion pairs and combinations.

In one embodiment of the system described herein, a RDE system is used with a model that predicts the response of the polarization curve to determine the concentrations of each ion in solution. In other embodiments, a static electrode is used, rather than a RDE. In embodiments in which more sensitivity is desired, an RDE is generally used, This method is very cheap and easy to use, it requires only 5-20 minutes, and its relationship is easy to follow. In certain embodiments, the detection limit is 1 ppm, which is comparable with other methods described above. For this process, the Fe (II) and Fe (III) can be modeled as linear equations, then using the two models, the Fe (II) and (III) concentrations in solution can be predicted simultaneously. The whole operation process is simple, and chemical agents are not needed during the analysis.

Description of the technique: In some embodiments, the system includes a rotating disk electrode and a potentiostat. The polarization curves are molded and the relationship or correlations found are functions of the concentration of the cations in solution. A rotating disk electrode consists of a disk of electrode material imbedded in a rod of an insulating material. The advantage of this electrode is that its steady state theory has been solved and the solution of the convective-diffusion equation is shown below:

$$i_r = 0.61\ nFAD^{5/6}\omega^{1/2}v^{-1/6}C$$

Which means that if the electrode arrangement is fixed and this process is controlled by the diffusion, then the limiting current linearly changes with the electrolyte concentration (C).

This technique is based upon the electrical properties of the cations in the solution. Electro-analytical techniques are capable of producing low detection limits and are specific for a particular oxidation state of the element (Fe (II) and Fe (III)), which makes it possible to determine the concentration of different oxidation state of the species in the same solution. For example, the redox reaction for Fe (II) and Fe (III) is given below:

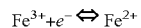
$$Fe^{3+} + e^- \Leftrightarrow Fe^{2+}$$

In this reaction, Fe (III) reduction to Fe (II) takes place at a lower potential, and the oxidation from Fe (II) to Fe (III) takes place at higher potential. The standard testing curve includes two limiting currents, which express the Fe (II) and Fe (III) concentration separately.

An inexpensive, simple, easy to use, accurate, and precise method to measure the concentration of multivalent cations (e.g., Fe(II)/Fe(III), As(III)/As(V), Se(IV)/Se(VI), Cr(VI)/Cr(III), and Sb(III)/Sb(V) and combinations thereof) simultaneously in solution have not been reported in the literature. Quantification of each of the different valances cations present in solution is very important for different process. For example, it has been reported that Fe(II) and Fe(III) have different effects on the electrolysis of coal, but an accurate method that allows to measure the concentrations of Fe(II) and Fe(III) is not available. The same thing happens in many other chemical process and biogeochemical systems. As described above, the current technique to determine Fe (II) and Fe (III) concentration in the same solution is time consuming, tedious and relative expensive. Here we develop a simple technique which can be used to measure the Fe (II) and Fe (III) ion simultaneously as well as any of the following cations: As(III)/As(V), Se(IV)/Se(VI), Cr(VI)/Cr(III), and Sb(III)/Sb(V).

Provided herein are: 1. An instrument to do this analysis; 2. a procedure to make the analysis; 3. models to calculate ion pair, such as Fe (II) and Fe (III), concentrations; and 4. the effect of different variables on the model and the technique.

The Instrument

Figure 2:
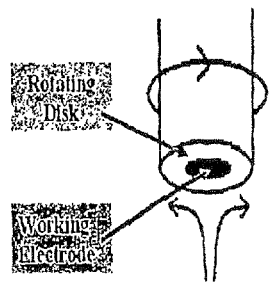
FIG. 2 shows a sketch of a rotating disk working electrode.

In one embodiment, this technique consists of using a rotating disk electrode (RDE) and a potentionstast. The RDE can be made as small as needed (for example, it could have the dimensions of a portable electric screw driver). In other embodiments, the electrode may be a static electrode. A Solartron polarization instrument was used for the experiments performed but the invention is not limited to this unique brand, any other potentiostact will work. The working electrode may be made of any electrode material that is compatible with the media. In some embodiments, the working electrode is a noble metal, in other embodiments, the working electrode may be a carbon electrode, such as glassy carbon, carbon fibers, carbon paper, or similar, in still other embodiments, the working electrode may include one or more layers of a noble metal on a carbon substrate. In an exemplary embodiment, the working electrode is made of Pt with an exposed area of 0.2 cm$^2$ mounted to a pine rotator (ATM SRX) shows in FIG. 1. FIG. 2 shows an exemplary rotating disk working electrode. A coiled platinum foil was used as the counter electrode and a saturated calomel electrode (Fisher Scientific) was used as reference electrode. The capillary used for the reference is lab made using a glass tube and wood chips filled with saturated KCl solution. The beaker which holds the solution is 200 mL (Fisher Scientific). The cyclic voltammetry was done by the Solartron 1287A, 1281 and 1252A. The software is CorrWare and the curve is easy to view using CorrView.

Exemplary Procedure for the Analysis

The following exemplary procedure, using Fe(II) and Fe(III) is used to illustrate the methods described herein. While it is shown for Fe(II)/Fe(III), it should be understood that this procedure may easily be adapted for other ion pairs or combinations of ions.

Preparation of the Solutions

In order to find the relationship between the limiting current and ion concentration, a standard solution was prepared as indicated below.

Ferric sulfate or Ferrous sulfate or both of them were measured (precision to 0.00001 g), then dissolved in distilled water. A fixed volume of sulfuric acid was dissolved into the same solution. This solution was then transferred to a long neck 100 ml flask, and the flask filled with distilled water to the 100 mL mark. Through this preparation, we can calculate the iron ion concentration. In this example, different concentrations of Fe (II) (Ferric sulfate) (from 0.1 ppm to 7000 ppm, Fe (III) (ferrous Sulfate) (from 0.1 ppm to 7000 ppm) and different ratios of Fe (III)/Fe (II) (From 0.1 ppm to 15000 ppm) were prepared. The sulfuric acid concentration was varied from 0.2 to 4M; the rotation rate was varied from 500 to 5000 rpm; and scan step changes were varied from 30 mV/s to 80 mV/s.

Figure 3:
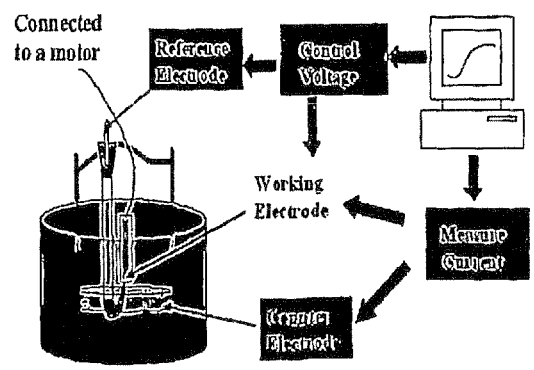
FIG. 3 shows an exemplary embodiment of the testing system.
Figure 4:
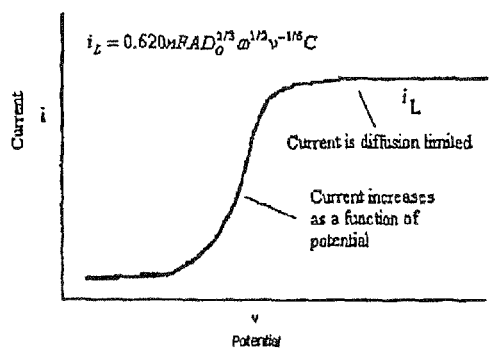
FIG. 4 shows current as a function of the applied potential.

CV Test for the Standard Solution:

FIG. 3 shows a schematic representation of the exemplary testing system. The potentiostat (Solartron) was used to apply a bias potentional to a saturated calomel electrode (SCE), and the current between the working electrode and the counter electrode were recorded in the computer. At the same time, the working electrode itself was rotated at a very high speed. This rotational motion sets up a well-defined flow of the solution towards the surface of the rotating disk electrode. The experimental results are generally plotted as a graph of current versus potential, and a typical rotating disk voltammogram exhibits a sigmoidal-shaped wave, and the height of this wave provides the analytical signal. The sigmoid wave height is often called the limiting current or Levich current (shown in FIG. 4). In other embodiments, the working electrode is a static electrode, rather than an RDE.

Choosing the Stable Curve

Figure 5:
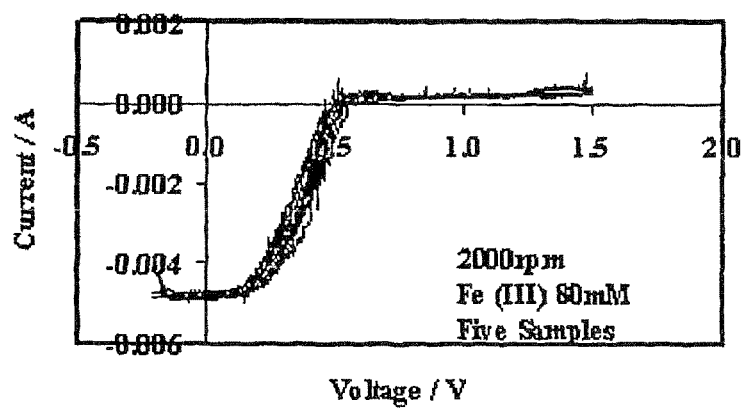
FIG. 5 shows the polarization curves for five samples of Fe(III) (after 9 cycles). The measurements are consistent (reproducible).
Figure 6:
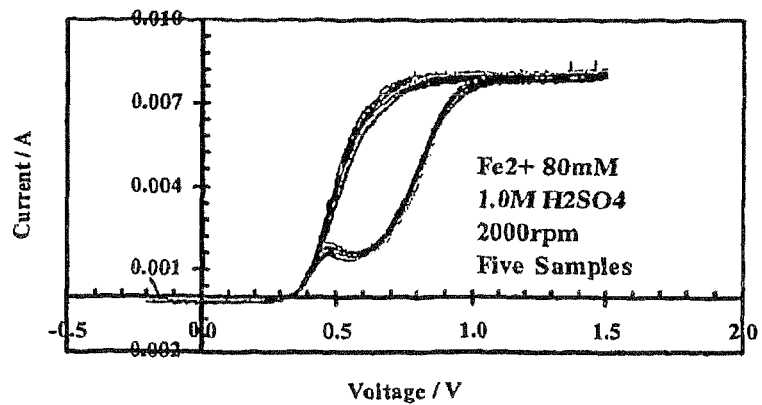
FIG. 6 shows the polarization curves for five samples of Fe(II) (after 9 cycles). The measurements are consistent (reproducible).
Figure 7:
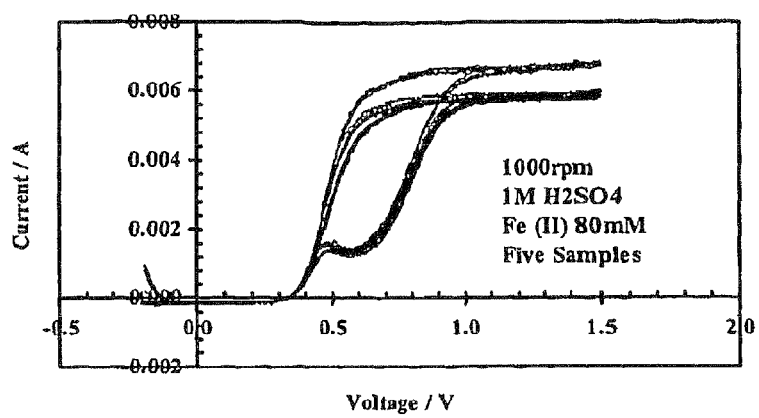
FIG. 7 shows polarization curves after three cycles for five samples of Fe (II).
Figure 8:
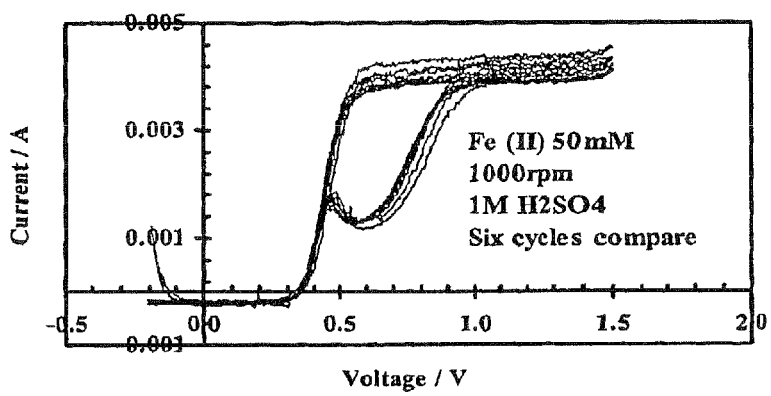
FIG. 8 shows polarization curves after six cycles for Fe(II). The first cycle is different.
Figure 9:
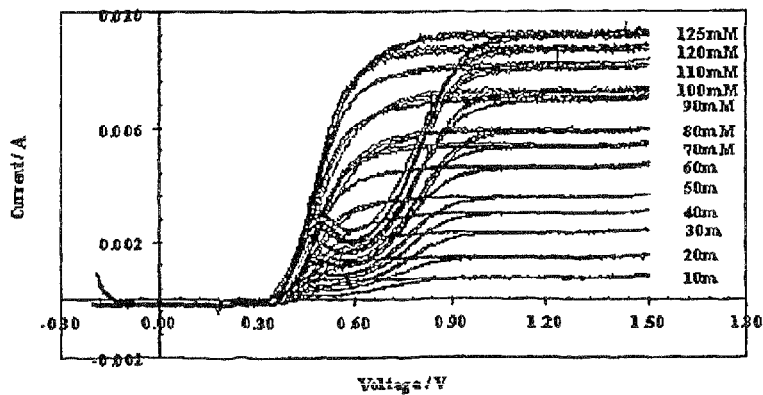
FIG. 9 shows the results of an exemplary 10 sample experimental results for different Fe (II) concentrations.
Figure 10:
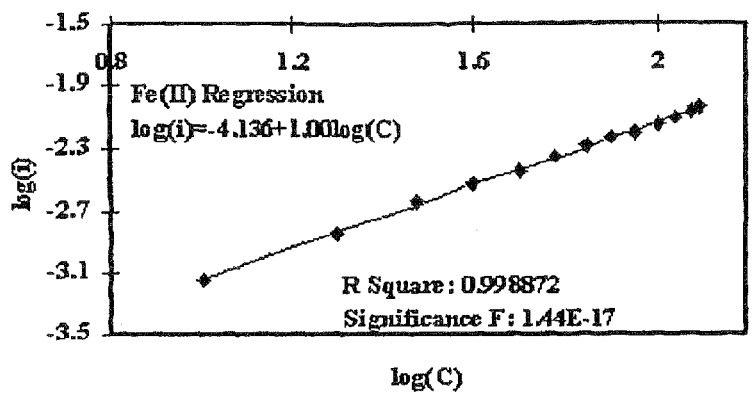
FIG. 10 shows the regression results for ten different concentrations of Fe (II) solutions, showing that the limiting current changes linearly with the concentration. The coefficient is equal to 1.
Figure 11:
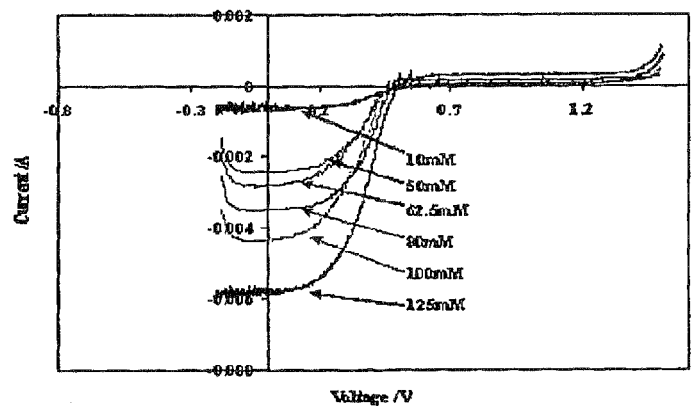
FIG. 11 shows the several sample experiments results for different Fe (II) concentrations.
Figure 12:
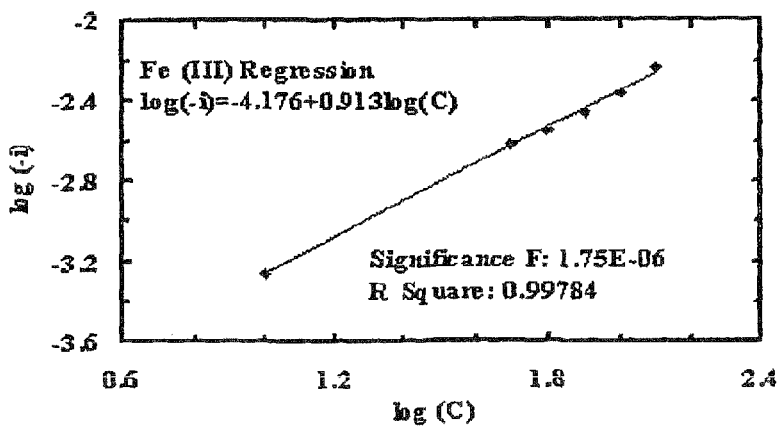
FIG. 12 shows the regression results for ten different concentrations of Fe (III) solutions, showing that the limiting current linearly changes with the concentration. The coefficient is equal to 1.

Most of the multivalent cations are not stable when open in the air. For example, the Fe (II) may oxide to Fe(III). Also before polarizing, the solution near the working electrode will get to an equilibrium, which will affect the first several cycles. FIGS. 5 to 7 show the results for five solution samples, after several cycles, the five samples have the same limiting current, except the error brought by the instrument or the experimental uncertainty. After the second cycle all polarization curves show the same behavior, the exception is for the first cycle, which indicates that the experiment should be run until the equilibrium is reached. Given longer time, the limiting currents will not change. FIG. 8 shows that first several cycles are not stable, and are not reproducible. According to the literature, the first cycles are trying to get the equilibrium for iron ion within the solution.

All the results show that there exists equilibrium between the solution with the air and the electrode, but when the potential increases, this balance changes. The same solution will come to a new equilibrium condition. Our object is to get the limiting current of the new equilibrium condition, for this is the stable and reproducible one. Therefore, the limiting currents of the reproducible cycles are the ones that will be needed for the method.

Model to Calculate Concentration of Cations

As an example the procedure used to develop the model to determine the concentration of Fe (II) and Fe (III) is shown. FIGS. 9-12 show the simulation results of the experiment data. It is clearly shown that the limiting currents of different concentration of Fe (II) and Fe (III) linearly change with their concentration, the linear equation $i_l = k_2 + k_3 \cdot C$ ($k_2$ and $k_3$ are the constants) can be used to describe this relationship. The constants are different for Fe (II) and Fe (III). The model constants will change depending on the system we used or the experimental condition (different working electrode, reference electrode, distance from capillary from working electrode, etc). Using the limiting current of the experiment and two linear equation models we can determine the concentration of Fe (II) and Fe (III).

Figure 13:
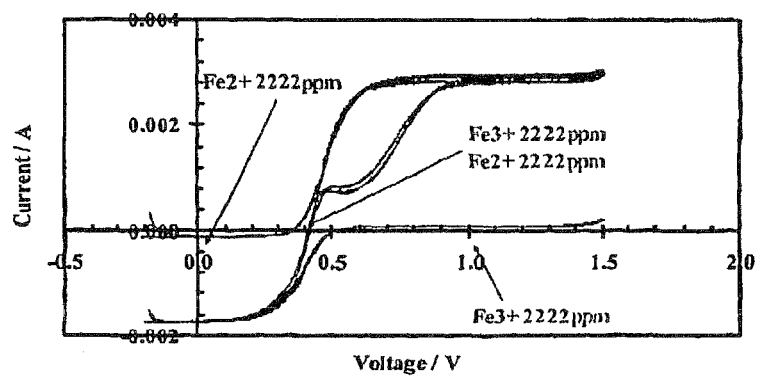
FIG. 13 shows that the limiting current relationship of equal-molar Fe (II)/Fe (III) with Fe (II) solution and Fe (III) solutions.
Figure 14:
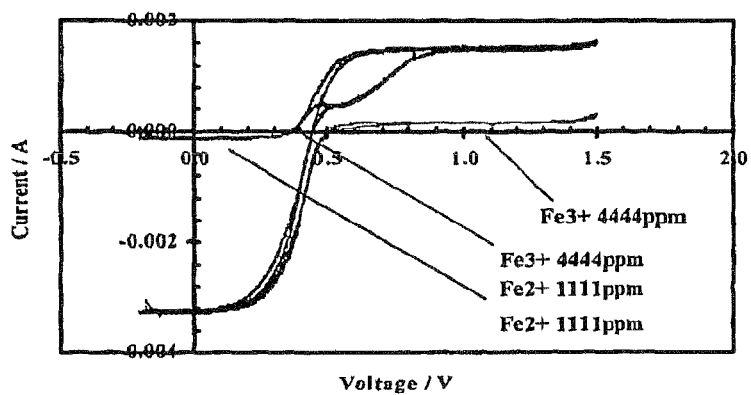
FIG. 14 shows the limiting current relationship for Fe (II) 1111 ppm/Fe (III) 4444 ppm solution with Fe (II) 1111 ppm and Fe (III) 4444 ppm solutions.
Figure 15:
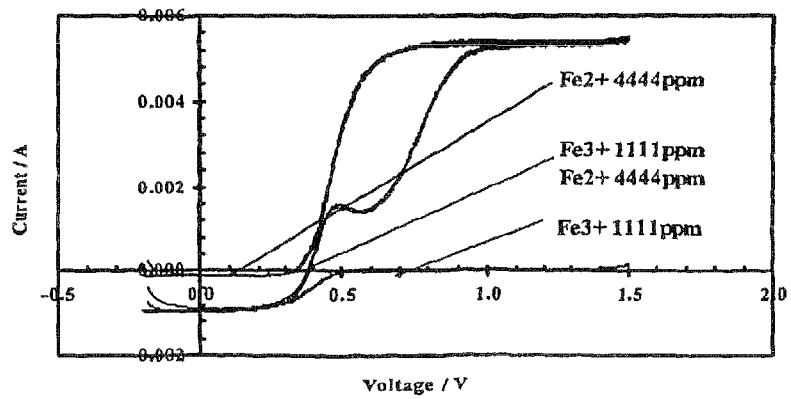
FIG. 15 shows the limiting current relationship for Fe (II) 4444 ppm/Fe (III) 1111 ppm solution with Fe (II) 4444 ppm and Fe (III) 1111 ppm solutions.

Determining the Fe (II) and Fe (III) concentrations simultaneously: FIGS. 13-15 show that the upper and lower limiting currents of the solution Fe (II)/Fe (III) correspond to the solution of the same concentration of Fe (II) and Fe (III). Those three figures showed the different ratio of Fe (II)/Fe (III), which shows that the ratio of the two ions will not affect the results. If we use enough of the sample solution, the two ions do not interact with each other for the CV, which allows the quantification of Fe (II)/Fe (III) simultaneously. So using the upper limiting currents for the Fe (II) model, we can get the Fe (II) concentration in the solution; using the lower limiting currents for the Fe (III) model, we can get the Fe (III) concentration in the solution.

Figure 16:
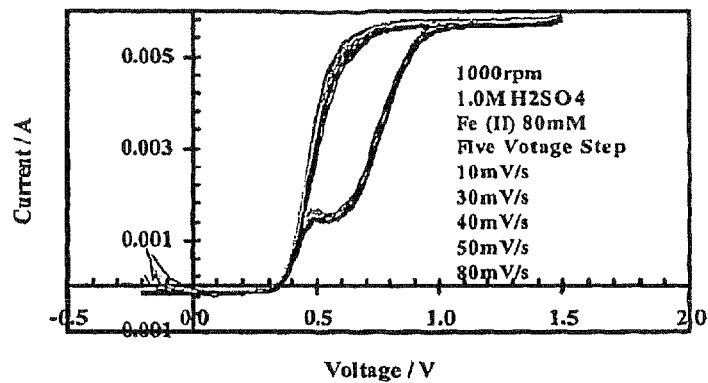
FIG. 16 shows the effect of the voltage step on the limiting current.

IV. Effect of Different Parameters on the Model—Effect of the Voltage Step:

FIG. 16 demonstrates that in our system, the voltage step (10 mV/s-80 mV/s) will not affect the limiting current. It will change the shape of the transition part of the curve a little, which does not affect our experimental results. This will bring many advantages when the method is applied. For example, if more data to analyze the process is desired, a smaller voltage step may be used, but if there are several solutions and we want to save time, we can use longer voltage step.

Effect of the Rotating Speed:

For the Rotating Disk Electrode (RDE) system, the limiting current equation is:

$$i_l = 0.61 \, nFAD^{5/6}\omega^{1/2}v^{-1/6}C \quad [1]$$

Where the $i_l$ is the limiting current of the solution, n is the number of electrons exchanged; F is the Faraday constant; A is the electrode surface area; D is the diffusion coefficient; ω is angular velocity of the rotation electrode; υ is the kinetic viscosity of the solution and C is the concentration of the solution.

Figure 17:
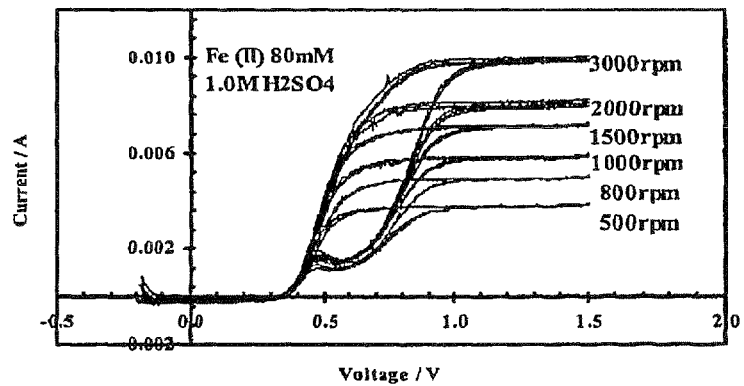
FIG. 17 shows the effect of rotation rate on the limiting current.

Our experimental results demonstrated this relationship: $i_l = k_1 \cdot \omega^{1/2}$ ($k_1$ is constant), which implies that the electrode reaction is a diffusion-controlled process. FIG. 17 shows the effect of the rotating speed on the limiting current. Increasing the rotation of the disk will increase the limiting current, which will give more accurate results when the concentration of the cations are small. Increasing the rotation rate properly will decrease the minimum concentration of iron ion. The rotation rate changes from 500 rpm to 3000 rpm, but higher than 3000 rpm will not guarantee the laminar flow near the working electrode which we will not use for our experiment. When high sensitivity is not needed, the working electrode may be a static electrode.

Effect of the Sulfuric Acid (Electrolyte) Concentration.

Figure 18:
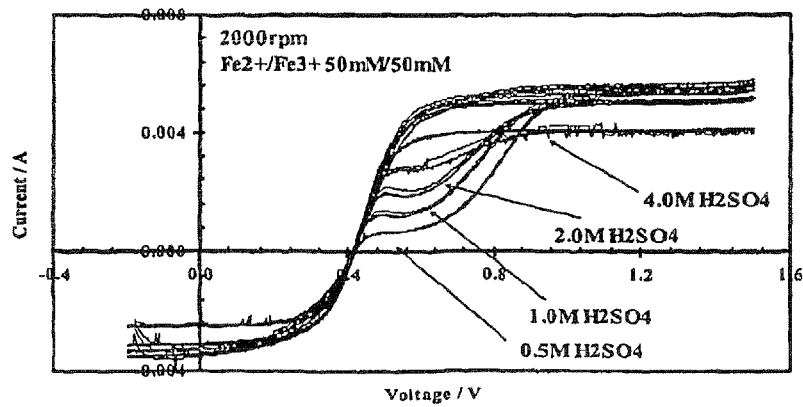
FIG. 18 shows the effect of sulfuric acid on the limiting current.

The sulfuric acid concentration is not a key factor that affects the limiting current, but the experiments showed that increasing the concentration of sulfuric acid will decrease the limiting current. The reason for this is that the interactions between the cations and the electrolyte become stronger. This decreases the mobility of the cations in the medium. Therefore it is recommended to work at low concentrations of the electrolyte. The experiments also show that higher than 1M concentration, the effect become apparent, but less than 1M, the effect is very small. FIG. 18 shows one set of experiments about the effect of the sulfuric acid concentration. Concentrations no higher than 1 M are recommended.

4. Effect of the Capillary.

Figure 19:
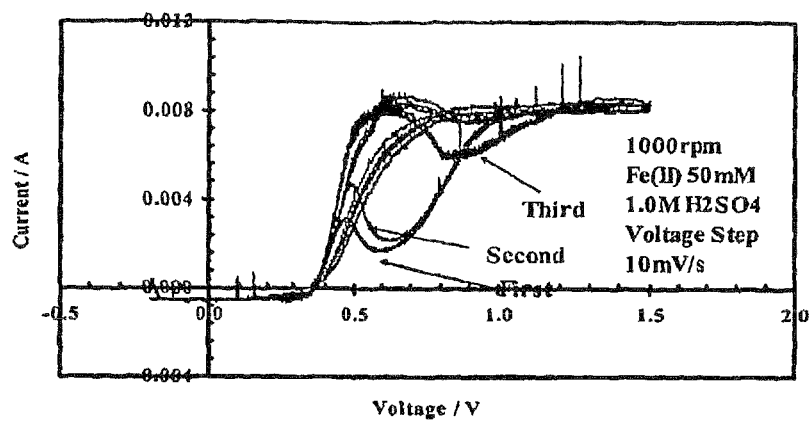
FIG. 19 shows the effect of the capillary on the limiting current. Capillary 3 has worse conducting condition, but the limiting current is consistency with the other two capillary.

The capillary insures that the reference works well. FIG. 19, shows the effect of different capillaries. The results indicate that disturbances are observed in the curve however, the limiting current does not change. So we can be sure that the capillary used in the experiment will not affect the accuracy of experimental result, but of course it will affect the precision of the results because of the capillary conducting condition. The worse conduction will make a lot noise which will make the curve have small waves or delay the time of the happening of the limiting current.

As described above the new features of the method described herein are clear: 1. this method is inexpensive and easy to use, it needs only 5-20 minutes, and its relationship is easy to follow. 2. By just doing one CV test for the sample solution, using the two or more models, we can easily determine the concentration of the multivalent cations simultaneously in the solution. 3. The whole operation process is simple, and no other agents are needed to aid this analysis. 4. The detection limit is 1 ppm, which is comparable with other methods.

The systems and methods described herein have significantly simplified the analysis procedure, decrease the cost and the most important advantages is that this new technique was based on the specific oxidation sate of the iron ion, which make it possible to measure the different oxidation state ion concentration at the same time within five minutes.

Electrodes

The working electrode needs to be cleaned after every experiment. The Pt counter electrode used in this experiment was found to work very well through one year of experiments. The capillary should be kept wet with saturated KCl solution in order to keep it working well, the same with the reference electrode. Other electrodes that can be used as working electrodes include glassy carbon, carbon fibers, carbon paper, and any other material inert to the media. In some embodiment, the counter electrode is Pt to have better accuracy and precision. In other embodiments, the counter electrode is another electrode material.

The examples described herein were conducted at room temperature (25° C.) and ambient pressure.

Practical Application

Figure 20:
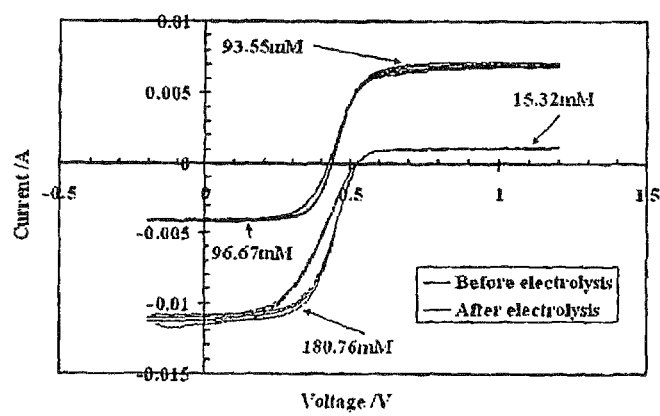
FIG. 20 shows an exemplary application of the technique for coal electrolysis.

One exemplary application of this method has been measuring Fe(II) and Fe(III) concentrations in solution before and after coal electrolysis. FIG. 20 shows the results for one experiment of coal electrolysis. These two curves show the analysis results before and after coal electrolysis. Using two model equations of Fe (II) and Fe (III), we calculate the concentration of Fe (II) and Fe (III) in the solution. Through this two analysis, we know that the Fe (II) also participates in to the oxidation process, which can be used to accurately determine $CO_2$ efficiency. This method may be used to measure the concentration of different multivalent cations in solution simultaneously, for example, Fe(II)/Fe(III), As(III)/As(V), Se(IV)/Se(VI), Cr(VI)/Cr(III), and Sb(III)/Sb(V) and combinations thereof. The unit can be mobile. The RDE can be made as small as a portable electric screw driver, and the system can utilize a static electrode, rather than a RDE.

The examples described herein are for illustration only and do not limit the scope of the invention as defined by the claims.

The invention claimed is:

1. A method for simultaneously measuring a concentration of a first cation having a first oxidative state and a concentration of a second cation having a second oxidative state that is different than the first oxidative state in a solution, the method comprising:
    a) applying a steady state polarization technique to the solution;
    b) simultaneously measuring both an upper limiting current and a lower limiting current of the solution during the steady state polarization technique; and
    c) correlating the measured upper limiting current with the concentration of the first cation and the measured lower limiting current with the concentration of the second cation.

2. The method of claim 1, wherein at least one of the first and second cations is a multivalent cation.

3. The method of claim 1, wherein the first and second cations are selected from the group consisting of Fe(II)/Fe(III), As(III)/As(V), Se(IV)/Se(VI), Cr(VI)/Cr(III), Sb(III)/Sb(V), and combinations thereof.

4. The method of claim 1, wherein the first cation is a first metal element at the first oxidative state and the second cation is a second metal element at the second oxidative state.

5. The method of claim 4, wherein the first and second cations are selected from the group consisting of Fe(II), Fe(III), As(III), As(V), Se(IV), Se(VI), Cr(VI), Cr(III), Sb(III), Sb(V), and combinations thereof.

6. The method of claim 1 further comprising:
    rotating and operating a disk electrode as a working electrode.

* * * * *